United States Patent [19]
Sharkey et al.

[11] Patent Number: 5,965,724
[45] Date of Patent: Oct. 12, 1999

[54] GP 130 LACKING THE TRANSMEMBRANE DOMAIN

[75] Inventors: Andrew Sharkey; Stephen Kevin Smith, both of Robinson Way; Kimberley Anne Dellow, London, all of United Kingdom

[73] Assignee: Applied Research Systems ARS Holding N.V., Curacao, Netherlands

[21] Appl. No.: 08/825,558

[22] Filed: Mar. 19, 1997

Related U.S. Application Data

[63] Continuation of application No. PCT/GB95/02243, Sep. 21, 1995, abandoned.

[30]   Foreign Application Priority Data

Sep. 21, 1994 [GB]   United Kingdom .................. 9419021

[51] Int. Cl.⁶ ........................... C12N 15/10; C12N 15/12; C07K 14/705
[52] U.S. Cl. .................... 536/23.5; 536/23.1; 435/320.1; 435/69.1; 530/350
[58] Field of Search ................................ 536/23.1, 23.5; 435/69.1, 320.1; 530/350, 351

[56]   References Cited

U.S. PATENT DOCUMENTS

| | | | |
|---|---|---|---|
| 5,132,403 | 7/1992 | Kishimoto | 530/351 |
| 5,223,611 | 6/1993 | Kishimoto | 530/351 |
| 5,426,048 | 6/1995 | Gearing et al. | 435/252.3 |
| 5,783,672 | 7/1998 | Mosley et al. | 53/350 |

FOREIGN PATENT DOCUMENTS

| | | |
|---|---|---|
| 0 411 946 A2 | 2/1991 | European Pat. Off. . |
| 6-22786 | 2/1985 | Japan . |
| WO 93/10151 | 5/1993 | WIPO . |
| WO 95/33059 | 12/1995 | WIPO . |
| WO 96/09382 | 3/1996 | WIPO . |

OTHER PUBLICATIONS

Geisterfer et al., Cytokines oncostatin M and interleukin 1 regulate the expression of the IL–6 receptor (gp80, and gp130), Cytokine, 7(6):503–9, Aug. 1995.
Hibi et al., Molecular cloning and expression of an IL–6 signal transducer, gp130, Cell, 63: 1149–57, Dec. 1990.
Adamson, E.D., "Activities of Growth Factors in Preimplantation Embryos," *J. Cell. Biochem.* 53:280–287 (Dec. 1993).
Harvey, M.B., and Kaye, P.L., "Insulin–Like Growth Factor–1 Stimulates Growth of Mouse Preimplantation Embryos In Vitro," *Mol. Reprod. Dev.* 31:195–199 (1992).
Hill, J.A., et al., "Products of Activated Lymphocytes and Macrophages Inhibit Mouse Embryo Development in Vitro," *J. Immunol.* 139(7):2250–2254 (1987).
Lachapelle, M.H., et al., "Embryonic resistance to tumour necrosis factor–α mediated cytotoxicity: novel mechanism underlying maternal immunological tolerance to the fetal allograft," *Human Reproduction* 8(7):1032–1038 (Jul. 1993).
Narazaki, M., et al., "Soluble Forms of the Interleukin–6 Signal–Transducing Receptor Component gp130 in Human Serum Possessing a Potential to Inhibit Signals Through Membrane–Anchored gp130," *Blood* 82(4):1120–1126 (Aug. 1993).
Pampfer, S., et al., "Expression of Tumor Necrosis Factor–α (TNFα) Receptors and Selective Effect of TNFα on the Inner Cell Mass in Mouse Blastocysts," *Endocrinology* 134 (1):206–212 (Jan. 1994).
Rappolee, D.A., et al., "Developmental Expression of PDGF, TGF–α, and TGF–β Genes in Preimplantation Mouse Embryos," *Science* 241:1823–1825 (1988).
Schultz, G.A., and Heyner, S., "Gene expression in pre–implantation mammalian embryos," *Mutation Research* 296:17–31 (1992).
Sharkey, A.M., et al., "Stage–Specific Expression of Cytokine and Receptor Messenger Ribonucleic Acids in Human Preimplantation Embryos," *Biol. Reprod.* 53:974–981 (Oct. 1995).
Taga, T., et al., "Functional inhibition of hematopoietic and neurotrophic cytokines by blocking the interleukin 6 signal transducer gp130," *Proc. Natl. Acad. Sci. USA* 89:10998–11001 (1992).
Watson, A.J., et al., "A Growth Factor Phenotype Map for Ovine Preimplantation Development," *Biol. Reprod.* 50:725–733 (Apr. 1994).
Witkin, S.S., et al., "Tumor necrosis factor is present in maternal sera and embryo culture fluids during in vitro fertilization," *J. Reprod. Immunol.* 19:85–93 (1991).
Yasukawa, K., et al., "Association of recombinant soluble IL–6–signal transducer, gp130, with a complex of IL 6 and soluble IL–6 receptor, and establishment of an ELISA for soluble gp130," *Immunology Letters* 31:123–130 (1992).
Zolti, M., et al., "Cytokine involvement in oocytes and early embryos," *Fertility and Sterility* 56(2):265–272 (1991).
English language abstract of Japanese Patent No. 06–22786, *Patent Abstracts of Japan* 18(226):C–1194 (Apr. 1994).
Copy of the International Search Report for International Application No. PCT/GB95/02243.

*Primary Examiner*—Lila Feisee
*Assistant Examiner*—Claire M. Kaufman
*Attorney, Agent, or Firm*—Sterne, Kessler, Goldstein & Fox P.L.L.C.

[57]   ABSTRACT

A novel splice-variant of gp 130 is disclosed, together with DNA sequence coding for it, pharmaceutical formulations comprising it, and its use ensuring the correct development of pre-implantation embryos.

3 Claims, 11 Drawing Sheets

FIG. 1

```
                                              5
                           Met Leu Thr Leu Gln Thr Trp
                           ATG TTG ACG TTG CAG ACT TGG 10                      15                      20
Val Val Gln Ala Leu Phe Ile Phe Leu Thr Thr Glu Ser Thr
GTA GTG CAA GCC TTG TTT ATT TTC CTC ACC ACT GAA TCT ACA 25                      30                      35
Gly Glu Leu Leu Asp Pro Cys Gly Tyr Ile Ser Pro Glu Ser
GGT GAA CTT CTA GAT CCA TGT GGT TAT ATC AGT CCT GAA TCT 40                      45
Pro Val Val Gln Leu His Ser Asn Phe Thr Ala Val Cys Val
CCA GTT GTA CAA CTT CAT TCT AAT TTC ACT GCA GTT TGT GTG 50                      55                      60
Leu Lys Glu Lys Cys Met Asp Tyr Phe His Val Asn Ala Asn
CTA AAG GAA AAA TGT ATG GAT TAT TTT CAT GTA AAT GCT AAT 65                      70                      75
Tyr Ile Val Trp Lys Thr Asn His Phe Thr Ile Pro Lys Glu
TAC ATT GTC TGG AAA ACA AAC CAT TTT ACT ATT CCT AAG GAG 80                      85                      90
Gln Tyr Thr Ile Ile Asn Arg Thr Ala Ser Ser Val Thr Phe
CAA TAT ACT ATC ATA AAC AGA ACA GCA TCC AGT GTC ACC TTT 95                      100                     105
Thr Asp Ile Ala Ser Leu Asn Ile Gln Leu Thr Cys Asn Ile
ACA GAT ATA GCT TCA TTA AAT ATT CAG CTC ACT TGC AAC ATT 110                     115
Leu Thr Phe Gly Gln Leu Glu Gln Asn Val Tyr Gly Ile Thr
CTT ACA TTC GGA CAG CTT GAA CAG AAT GTT TAT GGA ATC ACA 120                     125                     130
Ile Ile Ser Gly Leu Pro Pro Glu Lys Pro Lys Asn Leu Ser
ATA ATT TCA GGC TTG CCT CCA GAA AAA CCT AAA AAT TTG AGT
```

```
              135                           140                           145
Cys  Ile  Val  Asn  Glu  Gly  Lys  Lys  Met  Arg  Cys  Glu  Trp  Asp
TGC  ATT  GTG  AAC  GAG  GGG  AAG  AAA  ATG  AGG  TGT  GAG  TGG  GAT 150                           155                           160
Gly  Gly  Arg  Glu  Thr  His  Leu  Glu  Thr  Asn  Phe  Thr  Leu  Lys
GGT  GGA  AGG  GAA  ACA  CAC  TTG  GAG  ACA  AAC  TTC  ACT  TTA  AAA 165                           170                           175
Ser  Glu  Trp  Ala  Thr  His  Lys  Phe  Ala  Asp  Cys  Lys  Ala  Lys
TCT  GAA  TGG  GCA  ACA  CAC  AAG  TTT  GCT  GAT  TGC  AAA  GCA  AAA 180                           185
Arg  Asp  Thr  Pro  Thr  Ser  Cys  Thr  Val  Asp  Tyr  Ser  Thr  Val
CGT  GAC  ACC  CCC  ACC  TCA  TGC  ACT  GTT  GAT  TAT  TCT  ACT  GTG 190                      195                           200
Tyr  Phe  Val  Asn  Ile  Glu  Val  Trp  Val  Glu  Ala  Glu  Asn  Ala
TAT  TTT  GTC  AAC  ATT  GAA  GTC  TGG  GTA  GAA  GCA  GAG  AAT  GCC 205                           210                           215
Leu  Gly  Lys  Val  Thr  Ser  Asp  His  Ile  Asn  Phe  Asp  Pro  Val
CTT  GGG  AAG  GTT  ACA  TCA  GAT  CAT  ATC  AAT  TTT  GAT  CCT  GTA 220                           225                           230
Tyr  Lys  Val  Lys  Pro  Asn  Pro  Pro  His  Asn  Leu  Ser  Val  Ile
TAT  AAA  GTG  AAG  CCC  AAT  CCG  CCA  CAT  AAT  TTA  TCA  GTG  ATC 235                           240                           245
Asn  Ser  Glu  Glu  Leu  Ser  Ser  Ile  Leu  Lys  Leu  Thr  Trp  Thr
AAC  TCA  GAG  GAA  CTG  TCT  AGT  ATC  TTA  AAA  TTG  ACA  TGG  ACC 250                           255
Asn  Pro  Ser  Ile  Lys  Ser  Val  Ile  Ile  Leu  Lys  Tyr  Asn  Ile
AAC  CCA  AGT  ATT  AAG  AGT  GTT  ATA  ATA  CTA  AAA  TAT  AAC  ATT 260                      265                           270
Gln  Tyr  Arg  Thr  Lys  Asp  Ala  Ser  Thr  Trp  Ser  Gln  Ile  Pro
CAA  TAT  AGG  ACC  AAA  GAT  GCC  TCA  ACT  TGG  AGC  CAG  ATT  CCT 275                           280                           285
Pro  Glu  Asp  Thr  Ala  Ser  Thr  Arg  Ser  Ser  Phe  Thr  Val  Gln
CCT  GAA  GAC  ACA  GCA  TCC  ACC  CGA  TCT  TCA  TTC  ACT  GTC  CAA 290                           295                           300
Asp  Leu  Lys  Pro  Phe  Thr  Glu  Tyr  Val  Phe  Arg  Ile  Arg  Cys
GAC  CTT  AAA  CCT  TTT  ACA  GAA  TAT  GTG  TTT  AGG  ATT  CGC  TGT
```

```
                      305                         310                         315
Met Lys Glu Asp Gly Lys Gly Tyr Trp Ser Asp Trp Ser Glu
ATG AAG GAA GAT GGT AAG GGA TAC TGG AGT GAC TGG AGT GAA 320                         325
Glu Ala Ser Gly Ile Thr Tyr Glu Asp Arg Pro Ser Lys Ala
GAA GCA AGT GGG ATC ACC TAT GAA GAT AGA CCA TCT AAA GCA 330                         335                         340
Pro Ser Phe Trp Tyr Lys Ile Asp Pro Ser His Thr Gln Gly
CCA AGT TTC TGG TAT AAA ATA GAT CCA TCC CAT ACT CAA GGC 345                         350                         355
Tyr Arg Thr Val Gln Leu Val Trp Lys Thr Leu Pro Pro Phe
TAC AGA ACT GTA CAA CTC GTG TGG AAG ACA TTG CCT CCT TTT 360                         365                         370
Glu Ala Asn Gly Lys Ile Leu Asp Tyr Glu Val Thr Leu Thr
GAA GCC AAT GGA AAA ATC TTG GAT TAT GAA GTG ACT CTC ACA 375                         380                         385
Arg Trp Lys Ser His Leu Gln Asn Tyr Thr Val Asn Ala Thr
AGA TGG AAA TCA CAT TTA CAA AAT TAC ACA GTT AAT GCC ACA 390                         395
Lys Leu Thr Val Asn Leu Thr Asn Asp Arg Tyr Leu Ala Thr
AAA CTG ACA GTA AAT CTC ACA AAT GAT CGC TAT CTA GCA ACC 400                         405                         410
Leu Thr Val Arg Asn Leu Val Gly Lys Ser Asp Ala Ala Val
CTA ACA GTA AGA AAT CTT GTT GGC AAA TCA GAT GCA GCT GTT 415                         420                         425
Leu Thr Ile Pro Ala Cys Asp Phe Gln Ala Thr His Pro Val
TTA ACT ATC CCT GCC TGT GAC TTT CAA GCT ACT CAC CCT GTA 430                         435                         440
Met Asp Leu Lys Ala Phe Pro Lys Asp Asn Met Leu Trp Val
ATG GAT CTT AAA GCA TTC CCC AAA GAT AAC ATG CTT TGG GTG 445                         450                         455
Glu Trp Thr Thr Pro Arg Glu Ser Val Lys Lys Tyr Ile Leu
GAA TGG ACT ACT CCA AGG GAA TCT GTA AAG AAA TAT ATA CTT 460                         465
Glu Trp Cys Val Leu Ser Asp Lys Ala Pro Cys Ile Thr Asp
GAG TGG TGT GTG TTA TCA GAT AAA GCA CCC TGT ATC ACA GAC
```

```
470                         475                      480
Trp Gln Gln Glu Asp Gly Thr Val His Arg Thr Tyr Leu Arg
TGG CAA CAA GAA GAT GGT ACC GTG CAT CGC ACC TAT TTA AGA 485                      490                      495
Gly Asn Leu Ala Glu Ser Lys Cys Tyr Leu Ile Thr Val Thr
GGG AAC TTA GCA GAG AGC AAA TGC TAT TTG ATA ACA GTT ACT 500                      505                      510
Pro Val Tyr Ala Asp Gly Pro Gly Ser Pro Glu Ser Ile Lys
CCA GTA TAT GCT GAT GGA CCA GGA AGC CCT GAA TCC ATA AAG 515                      520                      525
Ala Tyr Leu Lys Gln Ala Pro Pro Ser Lys Gly Pro Thr Val
GCA TAC CTT AAA CAA GCT CCA CCT TCC AAA GGA CCT ACT GTT 530                      535
Arg Thr Lys Lys Val Gly Lys Asn Glu Ala Val Leu Glu Trp
CGG ACA AAA AAA GTA GGG AAA AAC GAA GCT GTC TTA GAG TGG 540                      545                      550
Asp Gln Leu Pro Val Asp Val Gln Asn Gly Phe Ile Arg Asn
GAC CAA CTT CCT GTT GAT GTT CAG AAT GGA TTT ATC AGA AAT 555                      560                      565
Tyr Thr Ile Phe Tyr Arg Thr Ile Ile Gly Asn Glu Thr Ala
TAT ACT ATA TTT TAT AGA ACC ATC ATT GGA AAT GAA ACT GCT 570                      575                      580
Val Asn Val Asp Ser Ser His Thr Glu Tyr Thr Leu Ser Ser
GTG AAT GTG GAT TCT TCC CAC ACA GAA TAT ACA TTG TCC TCT 585                      590                      595
Leu Thr Ser Asp Thr Leu Tyr Met Val Arg Met Ala Ala Tyr
TTG ACT AGT GAC ACA TTG TAC ATG GTA CGA ATG GCA GCA TAC 600                      605
Thr Asp Glu Gly Gly Lys Asp Gly Pro Glu Phe Thr Phe Thr
ACA GAT GAA GGT GGG AAG GAT GGT CCA GAA TTC ACT TTT ACT 610                      615                      620
Thr Pro Lys Phe Glu Leu Lys Asn Thr Ser Gly Leu Met Phe
ACC CCA AAG TTT GAA TTA AAA AAC ACA TCT GGC CTA ATG TTC 625                      630                      635
Gln Ile Leu Gln Arg Val Ile Leu Pro Ser Gly His Leu Thr
CAG ATC CTT CAA AGA GTC ATA TTG CCC AGT GGT CAC CTC ACA 640                      645                      650
Leu Leu Gln Gly Thr Ile Leu Ile Gln Lys Ile Lys Cys Ile
CTC CTC CAA GGC ACA ATT TTA ATT CAA AAG ATC AAA TGT ATT

655
Gln Met Ala Ile Ser Leu Met
CAG ATG GCA ATT TCA CTG ATG TAA
```

FIG. 2

```
                                              5
                        Met Leu Thr Leu Gln Thr Trp
                        ATG TTG ACG TTG CAG ACT TGG 10                    15                    20
Val Val Gln Ala Leu Phe Ile Phe Leu Thr Thr Glu Ser Thr
GTA GTG CAA GCC TTG TTT ATT TTC CTC ACC ACT GAA TCT ACA 25                    30                    35
Gly Glu Leu Leu Asp Pro Cys Gly Tyr Ile Ser Pro Glu Ser
GGT GAA CTT CTA GAT CCA TGT GGT TAT ATC AGT CCT GAA TCT 40                    45
Pro Val Val Gln Leu His Ser Asn Phe Thr Ala Val Cys Val
CCA GTT GTA CAA CTT CAT TCT AAT TTC ACT GCA GTT TGT GTG 50                     55                    60
Leu Lys Glu Lys Cys Met Asp Tyr Phe His Val Asn Ala Asn
CTA AAG GAA AAA TGT ATG GAT TAT TTT CAT GTA AAT GCT AAT 65                    70                    75
Tyr Ile Val Trp Lys Thr Asn His Phe Thr Ile Pro Lys Glu
TAC ATT GTC TGG AAA ACA AAC CAT TTT ACT ATT CCT AAG GAG 80                    85                    90
Gln Tyr Thr Ile Ile Asn Arg Thr Ala Ser Ser Val Thr Phe
CAA TAT ACT ATC ATA AAC AGA ACA GCA TCC AGT GTC ACC TTT 95                    100                   105
Thr Asp Ile Ala Ser Leu Asn Ile Gln Leu Thr Cys Asn Ile
ACA GAT ATA GCT TCA TTA AAT ATT CAG CTC ACT TGC AAC ATT 110                   115
Leu Thr Phe Gly Gln Leu Glu Gln Asn Val Tyr Gly Ile Thr
CTT ACA TTC GGA CAG CTT GAA CAG AAT GTT TAT GGA ATC ACA 120                     125                   130
Ile Ile Ser Gly Leu Pro Pro Glu Lys Pro Lys Asn Leu Ser
ATA ATT TCA GGC TTG CCT CCA GAA AAA CCT AAA AAT TTG AGT
```

```
         135                      140                      145
Cys Ile Val Asn Glu Gly Lys Lys Met Arg Cys Glu Trp Asp
TGC ATT GTG AAC GAG GGG AAG AAA ATG AGG TGT GAG TGG GAT 150                      155                      160
Gly Gly Arg Glu Thr His Leu Glu Thr Asn Phe Thr Leu Lys
GGT GGA AGG GAA ACA CAC TTG GAG ACA AAC TTC ACT TTA AAA 165                      170                      175
Ser Glu Trp Ala Thr His Lys Phe Ala Asp Cys Lys Ala Lys
TCT GAA TGG GCA ACA CAC AAG TTT GCT GAT TGC AAA GCA AAA 180                      185
Arg Asp Thr Pro Thr Ser Cys Thr Val Asp Tyr Ser Thr Val
CGT GAC ACC CCC ACC TCA TGC ACT GTT GAT TAT TCT ACT GTG 190                      195                      200
Tyr Phe Val Asn Ile Glu Val Trp Val Glu Ala Glu Asn Ala
TAT TTT GTC AAC ATT GAA GTC TGG GTA GAA GCA GAG AAT GCC 205                      210                      215
Leu Gly Lys Val Thr Ser Asp His Ile Asn Phe Asp Pro Val
CTT GGG AAG GTT ACA TCA GAT CAT ATC AAT TTT GAT CCT GTA 220                      225                      230
Tyr Lys Val Lys Pro Asn Pro Pro His Asn Leu Ser Val Ile
TAT AAA GTG AAG CCC AAT CCG CCA CAT AAT TTA TCA GTG ATC 235                      240                      245
Asn Ser Glu Glu Leu Ser Ser Ile Leu Lys Leu Thr Trp Thr
AAC TCA GAG GAA CTG TCT AGT ATC TTA AAA TTG ACA TGG ACC 250                      255
Asn Pro Ser Ile Lys Ser Val Ile Ile Leu Lys Tyr Asn Ile
AAC CCA AGT ATT AAG AGT GTT ATA ATA CTA AAA TAT AAC ATT 260                      265                      270
Gln Tyr Arg Thr Lys Asp Ala Ser Thr Trp Ser Gln Ile Pro
CAA TAT AGG ACC AAA GAT GCC TCA ACT TGG AGC CAG ATT CCT 275                      280                      285
Pro Glu Asp Thr Ala Ser Thr Arg Ser Ser Phe Thr Val Gln
CCT GAA GAC ACA GCA TCC ACC CGA TCT TCA TTC ACT GTC CAA 290                      295                      300
Asp Leu Lys Pro Phe Thr Glu Tyr Val Phe Arg Ile Arg Cys
GAC CTT AAA CCT TTT ACA GAA TAT GTG TTT AGG ATT CGC TGT
```

```
                              305                     310                     315
      Met Lys Glu Asp Gly Lys Gly Tyr Trp Ser Asp Trp Ser Glu
      ATG AAG GAA GAT GGT AAG GGA TAC TGG AGT GAC TGG AGT GAA 320                     325
      Glu Ala Ser Gly Ile Thr Tyr Glu Asp Arg Pro Ser Lys Ala
      GAA GCA AGT GGG ATC ACC TAT GAA GAT AGA CCA TCT AAA GCA 330                     335                     340
      Pro Ser Phe Trp Tyr Lys Ile Asp Pro Ser His Thr Gln Gly
      CCA AGT TTC TGG TAT AAA ATA GAT CCA TCC CAT ACT CAA GGC 345                     350                     355
      Tyr Arg Thr Val Gln Leu Val Trp Lys Thr Leu Pro Pro Phe
      TAC AGA ACT GTA CAA CTC GTG TGG AAG ACA TTG CCT CCT TTT 360                     365                     370
      Glu Ala Asn Gly Lys Ile Leu Asp Tyr Glu Val Thr Leu Thr
      GAA GCC AAT GGA AAA ATC TTG GAT TAT GAA GTG ACT CTC ACA 375                     380                     385
      Arg Trp Lys Ser His Leu Gln Asn Tyr Thr Val Asn Ala Thr
      AGA TGG AAA TCA CAT TTA CAA AAT TAC ACA GTT AAT GCC ACA 390                     395
      Lys Leu Thr Val Asn Leu Thr Asn Asp Arg Tyr Leu Ala Thr
      AAA CTG ACA GTA AAT CTC ACA AAT GAT CGC TAT CTA GCA ACC 400                     405                     410
      Leu Thr Val Arg Asn Leu Val Gly Lys Ser Asp Ala Ala Val
      CTA ACA GTA AGA AAT CTT GTT GGC AAA TCA GAT GCA GCT GTT 415                     420                     425
      Leu Thr Ile Pro Ala Cys Asp Phe Gln Ala Thr His Pro Val
      TTA ACT ATC CCT GCC TGT GAC TTT CAA GCT ACT CAC CCT GTA 430                     435                     440
      Met Asp Leu Lys Ala Phe Pro Lys Asp Asn Met Leu Trp Val
      ATG GAT CTT AAA GCA TTC CCC AAA GAT AAC ATG CTT TGG GTG 445                     450                     455
      Glu Trp Thr Thr Pro Arg Glu Ser Val Lys Lys Tyr Ile Leu
      GAA TGG ACT ACT CCA AGG GAA TCT GTA AAG AAA TAT ATA CTT 460                     465
      Glu Trp Cys Val Leu Ser Asp Lys Ala Pro Cys Ile Thr Asp
      GAG TGG TGT GTG TTA TCA GAT AAA GCA CCC TGT ATC ACA GAC
```

```
                                    470                          475                          480
      Trp  Gln  Gln  Glu  Asp  Gly  Thr  Val  His  Arg  Thr  Tyr  Leu  Arg
      TGG  CAA  CAA  GAA  GAT  GGT  ACC  GTG  CAT  CGC  ACC  TAT  TTA  AGA 485                          490                          495
      Gly  Asn  Leu  Ala  Glu  Ser  Lys  Cys  Tyr  Leu  Ile  Thr  Val  Thr
      GGG  AAC  TTA  GCA  GAG  AGC  AAA  TGC  TAT  TTG  ATA  ACA  GTT  ACT 500                          505                          510
      Pro  Val  Tyr  Ala  Asp  Gly  Pro  Gly  Ser  Pro  Glu  Ser  Ile  Lys
      CCA  GTA  TAT  GCT  GAT  GGA  CCA  GGA  AGC  CCT  GAA  TCC  ATA  AAG 515                          520                          525
      Ala  Tyr  Leu  Lys  Gln  Ala  Pro  Pro  Ser  Lys  Gly  Pro  Thr  Val
      GCA  TAC  CTT  AAA  CAA  GCT  CCA  CCT  TCC  AAA  GGA  CCT  ACT  GGT 530                          535
      Arg  Thr  Lys  Lys  Val  Gly  Lys  Asn  Glu  Ala  Val  Leu  Glu  Trp
      CGG  ACA  AAA  AAA  GTA  GGG  AAA  AAC  GAA  GCT  GTC  TTA  GAG  TGG 540                          545                          550
      Asp  Gln  Leu  Pro  Val  Asp  Val  Gln  Asn  Gly  Phe  Ile  Arg  Asn
      GAC  CAA  CTT  CCT  GTT  GAT  GTT  CAG  AAT  GGA  TTT  ATC  AGA  AAT 555                          560                          565
      Tyr  Thr  Ile  Phe  Tyr  Arg  Thr  Ile  Ile  Gly  Asn  Glu  Thr  Ala
      TAT  ACT  ATA  TTT  TAT  AGA  ACC  ATC  ATT  GGA  AAT  GAA  ACT  GCT 570                          575                          580
      Val  Asn  Val  Asp  Ser  Ser  His  Thr  Glu  Tyr  Thr  Leu  Ser  Ser
      GTG  AAT  GTG  GAT  TCT  TCC  CAC  ACA  GAA  TAT  ACA  TTG  TCC  TCT 585                          590                          595
      Leu  Thr  Ser  Asp  Thr  Leu  Tyr  Met  Val  Arg  Met  Ala  Ala  Tyr
      TTG  ACT  AGT  GAC  ACA  TTG  TAC  ATG  GTA  CGA  ATG  GCA  GCA  TAC 600                          605
      Thr  Asp  Glu  Gly  Gly  Lys  Asp  Gly  Pro  Glu  Phe  Thr  Phe  Thr
      ACA  GAT  GAA  GGT  GGG  AAG  GAT  GGT  CCA  GAA  TTC  ACT  TTT  ACT 610                          615                          620
      Thr  Pro  Lys  Phe  Ala  Gln  Gly  Glu  Ile  Glu  Ala  Ile  Val  Val
      ACC  CCA  AAG  TTT  GCT  CAA  GGA  GAA  ATT  GAA  GCC  ATA  GTC  GTG 625                          630                          635
      Pro  Val  Cys  Leu  Ala  Phe  Leu  Leu  Thr  Thr  Leu  Leu  Gly  Val
      CCT  GTT  TGC  TTA  GCA  TTC  CTA  TTG  ACA  ACT  CTT  CTG  GGA  GTG 640                          645                          650
      Leu  Phe  Cys  Phe  Asn  Lys  Arg  Asp  Leu  Ile  Lys  Lys  His  Ile
      CTG  TTC  TGC  TTT  AAT  AAG  CGA  GAC  CTA  ATT  AAA  AAA  CAC  ATC
```

```
                     655                        660                        665
      Trp Pro Asn Val Pro Asp Pro Ser Lys Ser His Ile Ala Gln
      TGG CCT AAT GTT CCA GAT CCT TCA AAG AGT CAT ATT GCC CAG 670                        675
      Trp Ser Pro His Thr Pro Pro Arg His Asn Phe Asn Ser Lys
      TGG TCA CCT CAC ACT CCT CCA AGG CAC AAT TTT AAT TCA AAA 680                        685                        690
  Asp Gln Met Tyr Ser Asp Gly Asn Phe Thr Asp Val Ser Val
  GAT CAA ATG TAT TCA GAT GGC AAT TTC ACT GAT GTA AGT GTT 695                        700                        705
  Val Glu Ile Glu Ala Asn Asp Lys Lys Pro Phe Pro Glu Asp
  GTG GAA ATA GAA GCA AAT GAC AAA AAG CCT TTT CCA GAA GAT 710                        715                        720
      Leu Lys Ser Leu Asp Leu Phe Lys Lys Glu Lys Ile Asn Thr
      CTG AAA TCA TTG GAC CTG TTC AAA AAG GAA AAA ATT AAT ACT 725                        730                        735
          Glu Gly His Ser Ser Gly Ile Gly Gly Ser Ser Cys Met Ser
          GAA GGA CAC AGC AGT GGT ATT GGG GGG TCT TCA TGC ATG TCA 740                        745
              Ser Ser Arg Pro Ser Ile Ser Ser Ser Asp Glu Asn Glu Ser
              TCT TCT AGG CCA AGC ATT TCT AGC AGT GAT GAA AAT GAA TCT 750                        755                        760
  Ser Gln Asn Thr Ser Ser Thr Val Gln Tyr Ser Thr Val Val
  TCA CAA AAC ACT TCG AGC ACT GTC CAG TAT TCT ACC GTG GTA 765                        770                        775
      His Ser Gly Tyr Arg His Gln Val Pro Ser Val Gln Val Phe
      CAC AGT GGC TAC AGA CAC CAA GTT CCG TCA GTC CAA GTC TTC 780                        785                        790
          Ser Arg Ser Glu Ser Thr Gln Pro Leu Leu Asp Ser Glu Glu
          TCA AGA TCC GAG TCT ACC CAG CCC TTG TTA GAT TCA GAG GAG 795                        800                        805
              Arg Pro Glu Asp Leu Gln Leu Val Asp His Val Asp Gly Gly
              CGG CCA GAA GAT CTA CAA TTA GTA GAT CAT GTA GAT GGC GGT
```

```
                    810                          815
Asp Gly Ile Leu Pro Arg Gln Gln Tyr Phe Lys Gln Asn Cys
GAT GGT ATT TTG CCC AGG CAA CAG TAC TTC AAA CAG AAC TGC 820                      825                      830
Ser Gln His Glu Ser Ser Pro Asp Ile Ser His Phe Glu Arg
AGT CAG CAT GAA TCC AGT CCA GAT ATT TCA CAT TTT GAA AGG 835                      840                      845
Ser Lys Gln Val Ser Ser Val Asn Glu Glu Asp Phe Val Arg
TCA AAG CAA GTT TCA TCA GTC AAT GAG GAA GAT TTT GTT AGA 850                      855                      860
Leu Lys Gln Gln Ile Ser Asp His Ile Ser Gln Ser Cys Gly
CTT AAA CAG CAG ATT TCA GAT CAT ATT TCA CAA TCC TGT GGA 865                      870                      875
Ser Gly Gln Met Lys Met Phe Gln Glu Val Ser Ala Ala Asp
TCT GGG CAA ATG AAA ATG TTT CAG GAA GTT TCT GCA GCA GAT 880                      885
Ala Phe Gly Pro Gly Thr Glu Gly Gln Val Glu Arg Phe Glu
GCT TTT GGT CCA GGT ACT GAG GGA CAA GTA GAA AGA TTT GAA 890                      895                      900
Thr Val Gly Met Glu Ala Ala Thr Asp Glu Gly Met Pro Lys
ACA GTT GGC ATG GAG GCT GCG ACT GAT GAA GGC ATG CCT AAA 905                      910                      915
Ser Tyr Leu Pro Gln Thr Val Arg Gln Gly Gly Tyr Met Pro
AGT TAC TTA CCA CAG ACT GTA CGG CAA GGC GGC TAC ATG CCT

918
Gln
CAG
```

FIG. 3

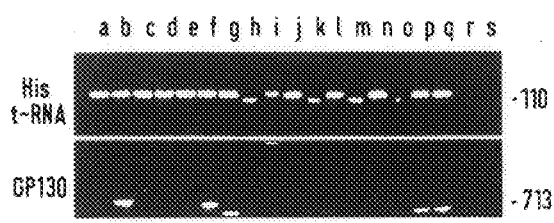

FIG. 4    PRIMERS USED FOR RT-PCR

| SPECIFICITY | PRIMER | SEQUENCE 5'→3' | FRAGMENT SIZE (bp) | POSITION ON cDNA | REFERENCE (cDNA SEQUENCE) |
|---|---|---|---|---|---|
| HistRS | EXTERNAL (5'END) | CCGCAGGTCGAGACAGC | | 518-534 | RABEN et al 1992 |
| | EXTERNAL (3'END) | CAAACACCTTCTCGCGAA | | 791-773 | NUCLEIC ACIDS RES |
| | INTERNAL (5'END) | CTTCAGGGAGAGCGCGTGC | | 595-613 | 20:1075-1081 |
| | INTERNAL (3'END) | TCATCAGGACCCAGCTGTGC | 110 | 704-685 | |
| gp130 | EXTERNAL (5'END) | TTGACTAGTGACACATTGTAC | | 1744-1764 | |
| | EXTERNAL (3'END) | TGAAACTTGCTTTGACCTTT | | 2514-2495 | HIBI et al 1990 |
| | INTERNAL (5'END) | GGTACGAATGGCAGCATACA | | 1767-1790 | CELL 63:1149-1157 |
| | INTERNAL (3'END) | CTGGACTGGATTCATGCTGA | 713 | 2480-2461 | |

SEQUENCE LISTING (1) GENERAL INFORMATION:

(iii) NUMBER OF SEQUENCES: 14

(2) INFORMATION FOR SEQ ID NO:1:

(i) SEQUENCE CHARACTERISTICS:
      (A) LENGTH: 45 amino acids
      (B) TYPE: amino acid
      (C) STRANDEDNESS: single
      (D) TOPOLOGY: Not Relevant (ii) MOLECULE TYPE: peptide (xi) SEQUENCE DESCRIPTION: SEQ ID NO:1:

```
Glu Leu Lys Asn Thr Ser Gly Leu Met Phe Gln Ile Leu Gln Arg Val
 1               5                  10                  15

Ile Leu Pro Ser Gly His Leu Thr Leu Leu Gln Gly Thr Ile Leu Ile
            20                  25                  30

Gln Lys Ile Lys Cys Ile Gln Met Ala Ile Ser Leu Met
        35                  40                  45
```

(2) INFORMATION FOR SEQ ID NO:2:

(i) SEQUENCE CHARACTERISTICS:
      (A) LENGTH: 138 base pairs
      (B) TYPE: nucleic acid
      (C) STRANDEDNESS: both
      (D) TOPOLOGY: linear (ii) MOLECULE TYPE: cDNA (xi) SEQUENCE DESCRIPTION: SEQ ID NO:2:

```
GAATTAAAAA ACACATCTGG CCTAATGTTC CAGATCCTTC AAAGAGTCAT ATTGCCCAGT     60

GGTCACCTCA CACTCCTCCA AGGCACAATT TTAATTCAAA AGATCAAATG TATTCAGATG    120

GCAATTTCAC TGATGTAA                                                  138
```

(2) INFORMATION FOR SEQ ID NO:3:

(i) SEQUENCE CHARACTERISTICS:
        (A) LENGTH: 1977 base pairs
        (B) TYPE: nucleic acid
        (C) STRANDEDNESS: both
        (D) TOPOLOGY: linear (ii) MOLECULE TYPE: cDNA (ix) FEATURE:
        (A) NAME/KEY: CDS
        (B) LOCATION: 1..1974

(xi) SEQUENCE DESCRIPTION: SEQ ID NO:3:

```
ATG TTG ACG TTG CAG ACT TGG GTA GTG CAA GCC TTG TTT ATT TTC CTC      48
Met Leu Thr Leu Gln Thr Trp Val Val Gln Ala Leu Phe Ile Phe Leu
1               5                   10                  15

ACC ACT GAA TCT ACA GGT GAA CTT CTA GAT CCA TGT GGT TAT ATC AGT      96
Thr Thr Glu Ser Thr Gly Glu Leu Leu Asp Pro Cys Gly Tyr Ile Ser
            20                  25                  30

CCT GAA TCT CCA GTT GTA CAA CTT CAT TCT AAT TTC ACT GCA GTT TGT     144
Pro Glu Ser Pro Val Val Gln Leu His Ser Asn Phe Thr Ala Val Cys
        35                  40                  45

GTG CTA AAG GAA AAA TGT ATG GAT TAT TTT CAT GTA AAT GCT AAT TAC     192
Val Leu Lys Glu Lys Cys Met Asp Tyr Phe His Val Asn Ala Asn Tyr
    50                  55                  60

ATT GTC TGG AAA ACA AAC CAT TTT ACT ATT CCT AAG GAG CAA TAT ACT     240
Ile Val Trp Lys Thr Asn His Phe Thr Ile Pro Lys Glu Gln Tyr Thr
65                  70                  75                  80

ATC ATA AAC AGA ACA GCA TCC AGT GTC ACC TTT ACA GAT ATA GCT TCA     288
Ile Ile Asn Arg Thr Ala Ser Ser Val Thr Phe Thr Asp Ile Ala Ser
                85                  90                  95

TTA AAT ATT CAG CTC ACT TGC AAC ATT CTT ACA TTC GGA CAG CTT GAA     336
Leu Asn Ile Gln Leu Thr Cys Asn Ile Leu Thr Phe Gly Gln Leu Glu
            100                 105                 110

CAG AAT GTT TAT GGA ATC ACA ATA ATT TCA GGC TTG CCT CCA GAA AAA     384
Gln Asn Val Tyr Gly Ile Thr Ile Ile Ser Gly Leu Pro Pro Glu Lys
        115                 120                 125

CCT AAA AAT TTG AGT TGC ATT GTG AAC GAG GGG AAG AAA ATG AGG TGT     432
Pro Lys Asn Leu Ser Cys Ile Val Asn Glu Gly Lys Lys Met Arg Cys
    130                 135                 140

GAG TGG GAT GGT GGA AGG GAA ACA CAC TTG GAG ACA AAC TTC ACT TTA     480
Glu Trp Asp Gly Gly Arg Glu Thr His Leu Glu Thr Asn Phe Thr Leu
145                 150                 155                 160

AAA TCT GAA TGG GCA ACA CAC AAG TTT GCT GAT TGC AAA GCA AAA CGT     528
Lys Ser Glu Trp Ala Thr His Lys Phe Ala Asp Cys Lys Ala Lys Arg
                165                 170                 175

GAC ACC CCC ACC TCA TGC ACT GTT GAT TAT TCT ACT GTG TAT TTT GTC     576
Asp Thr Pro Thr Ser Cys Thr Val Asp Tyr Ser Thr Val Tyr Phe Val
            180                 185                 190

AAC ATT GAA GTC TGG GTA GAA GCA GAG AAT GCC CTT GGG AAG GTT ACA     624
Asn Ile Glu Val Trp Val Glu Ala Glu Asn Ala Leu Gly Lys Val Thr
        195                 200                 205
```

```
TCA GAT CAT ATC AAT TTT GAT CCT GTA TAT AAA GTG AAG CCC AAT CCG        672
Ser Asp His Ile Asn Phe Asp Pro Val Tyr Lys Val Lys Pro Asn Pro
    210             215             220

CCA CAT AAT TTA TCA GTG ATC AAC TCA GAG GAA CTG TCT AGT ATC TTA        720
Pro His Asn Leu Ser Val Ile Asn Ser Glu Glu Leu Ser Ser Ile Leu
225             230             235                     240

AAA TTG ACA TGG ACC AAC CCA AGT ATT AAG AGT GTT ATA ATA CTA AAA        768
Lys Leu Thr Trp Thr Asn Pro Ser Ile Lys Ser Val Ile Ile Leu Lys
                245             250                     255

TAT AAC ATT CAA TAT AGG ACC AAA GAT GCC TCA ACT TGG AGC CAG ATT        816
Tyr Asn Ile Gln Tyr Arg Thr Lys Asp Ala Ser Thr Trp Ser Gln Ile
            260             265             270

CCT CCT GAA GAC ACA GCA TCC ACC CGA TCT TCA TTC ACT GTC CAA GAC        864
Pro Pro Glu Asp Thr Ala Ser Thr Arg Ser Ser Phe Thr Val Gln Asp
        275             280             285

CTT AAA CCT TTT ACA GAA TAT GTG TTT AGG ATT CGC TGT ATG AAG GAA        912
Leu Lys Pro Phe Thr Glu Tyr Val Phe Arg Ile Arg Cys Met Lys Glu
    290             295             300

GAT GGT AAG GGA TAC TGG AGT GAC TGG AGT GAA GAA GCA AGT GGG ATC        960
Asp Gly Lys Gly Tyr Trp Ser Asp Trp Ser Glu Glu Ala Ser Gly Ile
305             310             315                     320

ACC TAT GAA GAT AGA CCA TCT AAA GCA CCA AGT TTC TGG TAT AAA ATA       1008
Thr Tyr Glu Asp Arg Pro Ser Lys Ala Pro Ser Phe Trp Tyr Lys Ile
                325             330                     335

GAT CCA TCC CAT ACT CAA GGC TAC AGA ACT GTA CAA CTC GTG TGG AAG       1056
Asp Pro Ser His Thr Gln Gly Tyr Arg Thr Val Gln Leu Val Trp Lys
            340             345             350

ACA TTG CCT CCT TTT GAA GCC AAT GGA AAA ATC TTG GAT TAT GAA GTG       1104
Thr Leu Pro Pro Phe Glu Ala Asn Gly Lys Ile Leu Asp Tyr Glu Val
        355             360             365

ACT CTC ACA AGA TGG AAA TCA CAT TTA CAA AAT TAC ACA GTT AAT GCC       1152
Thr Leu Thr Arg Trp Lys Ser His Leu Gln Asn Tyr Thr Val Asn Ala
    370             375             380

ACA AAA CTG ACA GTA AAT CTC ACA AAT GAT CGC TAT CTA GCA ACC CTA       1200
Thr Lys Leu Thr Val Asn Leu Thr Asn Asp Arg Tyr Leu Ala Thr Leu
385             390             395                     400

ACA GTA AGA AAT CTT GTT GGC AAA TCA GAT GCA GCT GTT TTA ACT ATC       1248
Thr Val Arg Asn Leu Val Gly Lys Ser Asp Ala Ala Val Leu Thr Ile
                405             410                     415

CCT GCC TGT GAC TTT CAA GCT ACT CAC CCT GTA ATG GAT CTT AAA GCA       1296
Pro Ala Cys Asp Phe Gln Ala Thr His Pro Val Met Asp Leu Lys Ala
            420             425             430

TTC CCC AAA GAT AAC ATG CTT TGG GTG GAA TGG ACT ACT CCA AGG GAA       1344
Phe Pro Lys Asp Asn Met Leu Trp Val Glu Trp Thr Thr Pro Arg Glu
        435             440             445

TCT GTA AAG AAA TAT ATA CTT GAG TGG TGT GTG TTA TCA GAT AAA GCA       1392
Ser Val Lys Lys Tyr Ile Leu Glu Trp Cys Val Leu Ser Asp Lys Ala
    450             455             460

CCC TGT ATC ACA GAC TGG CAA CAA GAA GAT GGT ACC GTG CAT CGC ACC       1440
Pro Cys Ile Thr Asp Trp Gln Gln Glu Asp Gly Thr Val His Arg Thr
465             470             475                     480

TAT TTA AGA GGG AAC TTA GCA GAG AGC AAA TGC TAT TTG ATA ACA GTT       1488
Tyr Leu Arg Gly Asn Leu Ala Glu Ser Lys Cys Tyr Leu Ile Thr Val
                485             490                     495

ACT CCA GTA TAT GCT GAT GGA CCA GGA AGC CCT GAA TCC ATA AAG GCA       1536
Thr Pro Val Tyr Ala Asp Gly Pro Gly Ser Pro Glu Ser Ile Lys Ala
            500             505             510

TAC CTT AAA CAA GCT CCA CCT TCC AAA GGA CCT ACT GTT CGG ACA AAA       1584
Tyr Leu Lys Gln Ala Pro Pro Ser Lys Gly Pro Thr Val Arg Thr Lys
        515             520             525
```

| | | |
|---|---|---|
| AAA GTA GGG AAA AAC GAA GCT GTC TTA GAG TGG GAC CAA CTT CCT GTT<br>Lys Val Gly Lys Asn Glu Ala Val Leu Glu Trp Asp Gln Leu Pro Val<br>530                        535                      540 | 1632 |
| GAT GTT CAG AAT GGA TTT ATC AGA AAT TAT ACT ATA TTT TAT AGA ACC<br>Asp Val Gln Asn Gly Phe Ile Arg Asn Tyr Thr Ile Phe Tyr Arg Thr<br>545                       550                      555              560 | 1680 |
| ATC ATT GGA AAT GAA ACT GCT GTG AAT GTG GAT TCT TCC CAC ACA GAA<br>Ile Ile Gly Asn Glu Thr Ala Val Asn Val Asp Ser Ser His Thr Glu<br>                    565                      570                      575 | 1728 |
| TAT ACA TTG TCC TCT TTG ACT AGT GAC ACA TTG TAC ATG GTA CGA ATG<br>Tyr Thr Leu Ser Ser Leu Thr Ser Asp Thr Leu Tyr Met Val Arg Met<br>            580                      585                      590 | 1776 |
| GCA GCA TAC ACA GAT GAA GGT GGG AAG GAT GGT CCA GAA TTC ACT TTT<br>Ala Ala Tyr Thr Asp Glu Gly Gly Lys Asp Gly Pro Glu Phe Thr Phe<br>                595                      600                      605 | 1824 |
| ACT ACC CCA AAG TTT GAA TTA AAA AAC ACA TCT GGC CTA ATG TTC CAG<br>Thr Thr Pro Lys Phe Glu Leu Lys Asn Thr Ser Gly Leu Met Phe Gln<br>610                        615                      620 | 1872 |
| ATC CTT CAA AGA GTC ATA TTG CCC AGT GGT CAC CTC ACA CTC CTC CAA<br>Ile Leu Gln Arg Val Ile Leu Pro Ser Gly His Leu Thr Leu Leu Gln<br>625                        630                      635              640 | 1920 |
| GGC ACA ATT TTA ATT CAA AAG ATC AAA TGT ATT CAG ATG GCA ATT TCA<br>Gly Thr Ile Leu Ile Gln Lys Ile Lys Cys Ile Gln Met Ala Ile Ser<br>                    645                      650                      655 | 1968 |
| CTG ATG TAA<br>Leu Met | 1977 |

(2) INFORMATION FOR SEQ ID NO:4:

(i) SEQUENCE CHARACTERISTICS:
        (A) LENGTH: 658 amino acids
        (B) TYPE: amino acid
        (D) TOPOLOGY: linear (ii) MOLECULE TYPE: protein (xi) SEQUENCE DESCRIPTION: SEQ ID NO:4:

```
Met Leu Thr Leu Gln Thr Trp Val Val Gln Ala Leu Phe Ile Phe Leu
  1               5                  10                  15

Thr Thr Glu Ser Thr Gly Glu Leu Leu Asp Pro Cys Gly Tyr Ile Ser
             20                  25                  30

Pro Glu Ser Pro Val Val Gln Leu His Ser Asn Phe Thr Ala Val Cys
         35                  40                  45

Val Leu Lys Glu Lys Cys Met Asp Tyr Phe His Val Asn Ala Asn Tyr
 50                  55                  60

Ile Val Trp Lys Thr Asn His Phe Thr Ile Pro Lys Glu Gln Tyr Thr
 65                  70                  75                  80

Ile Ile Asn Arg Thr Ala Ser Ser Val Thr Phe Thr Asp Ile Ala Ser
             85                  90                  95

Leu Asn Ile Gln Leu Thr Cys Asn Ile Leu Thr Phe Gly Gln Leu Glu
        100                 105                 110

Gln Asn Val Tyr Gly Ile Thr Ile Ile Ser Gly Leu Pro Pro Glu Lys
        115                 120                 125

Pro Lys Asn Leu Ser Cys Ile Val Asn Glu Gly Lys Lys Met Arg Cys
130                 135                 140

Glu Trp Asp Gly Gly Arg Glu Thr His Leu Glu Thr Asn Phe Thr Leu
145                 150                 155                 160

Lys Ser Glu Trp Ala Thr His Lys Phe Ala Asp Cys Lys Ala Lys Arg
            165                 170                 175
```

-continued

```
Asp Thr Pro Thr Ser Cys Thr Val Asp Tyr Ser Thr Val Tyr Phe Val
            180                 185                 190

Asn Ile Glu Val Trp Val Glu Ala Glu Asn Ala Leu Gly Lys Val Thr
        195                 200                 205

Ser Asp His Ile Asn Phe Asp Pro Val Tyr Lys Val Lys Pro Asn Pro
210                 215                 220

Pro His Asn Leu Ser Val Ile Asn Ser Glu Glu Leu Ser Ser Ile Leu
225                 230                 235                 240

Lys Leu Thr Trp Thr Asn Pro Ser Ile Lys Ser Val Ile Ile Leu Lys
            245                 250                 255

Tyr Asn Ile Gln Tyr Arg Thr Lys Asp Ala Ser Thr Trp Ser Gln Ile
            260                 265                 270

Pro Pro Glu Asp Thr Ala Ser Thr Arg Ser Ser Phe Thr Val Gln Asp
            275                 280                 285

Leu Lys Pro Phe Thr Glu Tyr Val Phe Arg Ile Arg Cys Met Lys Glu
290                 295                 300

Asp Gly Lys Gly Tyr Trp Ser Asp Trp Ser Glu Glu Ala Ser Gly Ile
305                 310                 315                 320

Thr Tyr Glu Asp Arg Pro Ser Lys Ala Pro Ser Phe Trp Tyr Lys Ile
            325                 330                 335

Asp Pro Ser His Thr Gln Gly Tyr Arg Thr Val Gln Leu Val Trp Lys
            340                 345                 350

Thr Leu Pro Pro Phe Glu Ala Asn Gly Lys Ile Leu Asp Tyr Glu Val
            355                 360                 365

Thr Leu Thr Arg Trp Lys Ser His Leu Gln Asn Tyr Thr Val Asn Ala
            370                 375                 380

Thr Lys Leu Thr Val Asn Leu Thr Asn Asp Arg Tyr Leu Ala Thr Leu
385                 390                 395                 400

Thr Val Arg Asn Leu Val Gly Lys Ser Asp Ala Ala Val Leu Thr Ile
            405                 410                 415

Pro Ala Cys Asp Phe Gln Ala Thr His Pro Val Met Asp Leu Lys Ala
            420                 425                 430

Phe Pro Lys Asp Asn Met Leu Trp Val Glu Trp Thr Thr Pro Arg Glu
            435                 440                 445

Ser Val Lys Lys Tyr Ile Leu Glu Trp Cys Val Leu Ser Asp Lys Ala
450                 455                 460

Pro Cys Ile Thr Asp Trp Gln Gln Glu Asp Gly Thr Val His Arg Thr
465                 470                 475                 480

Tyr Leu Arg Gly Asn Leu Ala Glu Ser Lys Cys Tyr Leu Ile Thr Val
            485                 490                 495

Thr Pro Val Tyr Ala Asp Gly Pro Gly Ser Pro Glu Ser Ile Lys Ala
            500                 505                 510

Tyr Leu Lys Gln Ala Pro Pro Ser Lys Gly Pro Thr Val Arg Thr Lys
            515                 520                 525

Lys Val Gly Lys Asn Glu Ala Val Leu Glu Trp Asp Gln Leu Pro Val
            530                 535                 540

Asp Val Gln Asn Gly Phe Ile Arg Asn Tyr Thr Ile Phe Tyr Arg Thr
545                 550                 555                 560

Ile Ile Gly Asn Glu Thr Ala Val Asn Val Asp Ser Ser His Thr Glu
            565                 570                 575

Tyr Thr Leu Ser Ser Leu Thr Ser Asp Thr Leu Tyr Met Val Arg Met
            580                 585                 590

Ala Ala Tyr Thr Asp Glu Gly Gly Lys Asp Gly Pro Glu Phe Thr Phe
            595                 600                 605
```

```
Thr Thr Pro Lys Phe Glu Leu Lys Asn Thr Ser Gly Leu Met Phe Gln
        610                 615                 620

Ile Leu Gln Arg Val Ile Leu Pro Ser Gly His Leu Thr Leu Leu Gln
625                 630                 635                 640

Gly Thr Ile Leu Ile Gln Lys Ile Lys Cys Ile Gln Met Ala Ile Ser
                645                 650                 655

Leu Met (2) INFORMATION FOR SEQ ID NO:5:

(i) SEQUENCE CHARACTERISTICS:
        (A) LENGTH: 2754 base pairs
        (B) TYPE: nucleic acid
        (C) STRANDEDNESS: both
        (D) TOPOLOGY: linear (ii) MOLECULE TYPE: cDNA (ix) FEATURE:
        (A) NAME/KEY: CDS
        (B) LOCATION: 1..2754

(xi) SEQUENCE DESCRIPTION: SEQ ID NO:5:

ATG TTG ACG TTG CAG ACT TGG GTA GTG CAA GCC TTG TTT ATT TTC CTC      48
Met Leu Thr Leu Gln Thr Trp Val Val Gln Ala Leu Phe Ile Phe Leu
 1               5                  10                  15

ACC ACT GAA TCT ACA GGT GAA CTT CTA GAT CCA TGT GGT TAT ATC AGT      96
Thr Thr Glu Ser Thr Gly Glu Leu Leu Asp Pro Cys Gly Tyr Ile Ser
                20                  25                  30

CCT GAA TCT CCA GTT GTA CAA CTT CAT TCT AAT TTC ACT GCA GTT TGT     144
Pro Glu Ser Pro Val Val Gln Leu His Ser Asn Phe Thr Ala Val Cys
            35                  40                  45

GTG CTA AAG GAA AAA TGT ATG GAT TAT TTT CAT GTA AAT GCT AAT TAC     192
Val Leu Lys Glu Lys Cys Met Asp Tyr Phe His Val Asn Ala Asn Tyr
        50                  55                  60

ATT GTC TGG AAA ACA AAC CAT TTT ACT ATT CCT AAG GAG CAA TAT ACT     240
Ile Val Trp Lys Thr Asn His Phe Thr Ile Pro Lys Glu Gln Tyr Thr
65                  70                  75                  80

ATC ATA AAC AGA ACA GCA TCC AGT GTC ACC TTT ACA GAT ATA GCT TCA     288
Ile Ile Asn Arg Thr Ala Ser Ser Val Thr Phe Thr Asp Ile Ala Ser
                85                  90                  95

TTA AAT ATT CAG CTC ACT TGC AAC ATT CTT ACA TTC GGA CAG CTT GAA     336
Leu Asn Ile Gln Leu Thr Cys Asn Ile Leu Thr Phe Gly Gln Leu Glu
            100                 105                 110

CAG AAT GTT TAT GGA ATC ACA ATA ATT TCA GGC TTG CCT CCA GAA AAA     384
Gln Asn Val Tyr Gly Ile Thr Ile Ile Ser Gly Leu Pro Pro Glu Lys
        115                 120                 125

CCT AAA AAT TTG AGT TGC ATT GTG AAC GAG GGG AAG AAA ATG AGG TGT     432
Pro Lys Asn Leu Ser Cys Ile Val Asn Glu Gly Lys Lys Met Arg Cys
130                 135                 140

GAG TGG GAT GGT GGA AGG GAA ACA CAC TTG GAG ACA AAC TTC ACT TTA     480
Glu Trp Asp Gly Gly Arg Glu Thr His Leu Glu Thr Asn Phe Thr Leu
145                 150                 155                 160

AAA TCT GAA TGG GCA ACA CAC AAG TTT GCT GAT TGC AAA GCA AAA CGT     528
Lys Ser Glu Trp Ala Thr His Lys Phe Ala Asp Cys Lys Ala Lys Arg
                165                 170                 175

GAC ACC CCC ACC TCA TGC ACT GTT GAT TAT TCT ACT GTG TAT TTT GTC     576
Asp Thr Pro Thr Ser Cys Thr Val Asp Tyr Ser Thr Val Tyr Phe Val
            180                 185                 190

AAC ATT GAA GTC TGG GTA GAA GCA GAG AAT GCC CTT GGG AAG GTT ACA     624
Asn Ile Glu Val Trp Val Glu Ala Glu Asn Ala Leu Gly Lys Val Thr
        195                 200                 205
```

```
TCA GAT CAT ATC AAT TTT GAT CCT GTA TAT AAA GTG AAG CCC AAT CCG    672
Ser Asp His Ile Asn Phe Asp Pro Val Tyr Lys Val Lys Pro Asn Pro
    210                 215                 220

CCA CAT AAT TTA TCA GTG ATC AAC TCA GAG GAA CTG TCT AGT ATC TTA    720
Pro His Asn Leu Ser Val Ile Asn Ser Glu Glu Leu Ser Ser Ile Leu
225                 230                 235                 240

AAA TTG ACA TGG ACC AAC CCA AGT ATT AAG AGT GTT ATA ATA CTA AAA    768
Lys Leu Thr Trp Thr Asn Pro Ser Ile Lys Ser Val Ile Ile Leu Lys
                245                 250                 255

TAT AAC ATT CAA TAT AGG ACC AAA GAT GCC TCA ACT TGG AGC CAG ATT    816
Tyr Asn Ile Gln Tyr Arg Thr Lys Asp Ala Ser Thr Trp Ser Gln Ile
            260                 265                 270

CCT CCT GAA GAC ACA GCA TCC ACC CGA TCT TCA TTC ACT GTC CAA GAC    864
Pro Pro Glu Asp Thr Ala Ser Thr Arg Ser Ser Phe Thr Val Gln Asp
        275                 280                 285

CTT AAA CCT TTT ACA GAA TAT GTG TTT AGG ATT CGC TGT ATG AAG GAA    912
Leu Lys Pro Phe Thr Glu Tyr Val Phe Arg Ile Arg Cys Met Lys Glu
    290                 295                 300

GAT GGT AAG GGA TAC TGG AGT GAC TGG AGT GAA GAA GCA AGT GGG ATC    960
Asp Gly Lys Gly Tyr Trp Ser Asp Trp Ser Glu Glu Ala Ser Gly Ile
305                 310                 315                 320

ACC TAT GAA GAT AGA CCA TCT AAA GCA CCA AGT TTC TGG TAT AAA ATA   1008
Thr Tyr Glu Asp Arg Pro Ser Lys Ala Pro Ser Phe Trp Tyr Lys Ile
                325                 330                 335

GAT CCA TCC CAT ACT CAA GGC TAC AGA ACT GTA CAA CTC GTG TGG AAG   1056
Asp Pro Ser His Thr Gln Gly Tyr Arg Thr Val Gln Leu Val Trp Lys
            340                 345                 350

ACA TTG CCT CCT TTT GAA GCC AAT GGA AAA ATC TTG GAT TAT GAA GTG   1104
Thr Leu Pro Pro Phe Glu Ala Asn Gly Lys Ile Leu Asp Tyr Glu Val
        355                 360                 365

ACT CTC ACA AGA TGG AAA TCA CAT TTA CAA AAT TAC ACA GTT AAT GCC   1152
Thr Leu Thr Arg Trp Lys Ser His Leu Gln Asn Tyr Thr Val Asn Ala
    370                 375                 380

ACA AAA CTG ACA GTA AAT CTC ACA AAT GAT CGC TAT CTA GCA ACC CTA   1200
Thr Lys Leu Thr Val Asn Leu Thr Asn Asp Arg Tyr Leu Ala Thr Leu
385                 390                 395                 400

ACA GTA AGA AAT CTT GTT GGC AAA TCA GAT GCA GCT GTT TTA ACT ATC   1248
Thr Val Arg Asn Leu Val Gly Lys Ser Asp Ala Ala Val Leu Thr Ile
                405                 410                 415

CCT GCC TGT GAC TTT CAA GCT ACT CAC CCT GTA ATG GAT CTT AAA GCA   1296
Pro Ala Cys Asp Phe Gln Ala Thr His Pro Val Met Asp Leu Lys Ala
            420                 425                 430

TTC CCC AAA GAT AAC ATG CTT TGG GTG GAA TGG ACT ACT CCA AGG GAA   1344
Phe Pro Lys Asp Asn Met Leu Trp Val Glu Trp Thr Thr Pro Arg Glu
        435                 440                 445

TCT GTA AAG AAA TAT ATA CTT GAG TGG TGT GTG TTA TCA GAT AAA GCA   1392
Ser Val Lys Lys Tyr Ile Leu Glu Trp Cys Val Leu Ser Asp Lys Ala
    450                 455                 460

CCC TGT ATC ACA GAC TGG CAA CAA GAA GAT GGT ACC GTG CAT CGC ACC   1440
Pro Cys Ile Thr Asp Trp Gln Gln Glu Asp Gly Thr Val His Arg Thr
465                 470                 475                 480

TAT TTA AGA GGG AAC TTA GCA GAG AGC AAA TGC TAT TTG ATA ACA GTT   1488
Tyr Leu Arg Gly Asn Leu Ala Glu Ser Lys Cys Tyr Leu Ile Thr Val
                485                 490                 495

ACT CCA GTA TAT GCT GAT GGA CCA GGA AGC CCT GAA TCC ATA AAG GCA   1536
Thr Pro Val Tyr Ala Asp Gly Pro Gly Ser Pro Glu Ser Ile Lys Ala
            500                 505                 510

TAC CTT AAA CAA GCT CCA CCT TCC AAA GGA CCT ACT GGT CGG ACA AAA   1584
Tyr Leu Lys Gln Ala Pro Pro Ser Lys Gly Pro Thr Gly Arg Thr Lys
    515                 520                 525
```

```
AAA GTA GGG AAA AAC GAA GCT GTC TTA GAG TGG GAC CAA CTT CCT GTT        1632
Lys Val Gly Lys Asn Glu Ala Val Leu Glu Trp Asp Gln Leu Pro Val
        530                 535                 540

GAT GTT CAG AAT GGA TTT ATC AGA AAT TAT ACT ATA TTT TAT AGA ACC        1680
Asp Val Gln Asn Gly Phe Ile Arg Asn Tyr Thr Ile Phe Tyr Arg Thr
545                 550                 555                 560

ATC ATT GGA AAT GAA ACT GCT GTG AAT GTG GAT TCT TCC CAC ACA GAA        1728
Ile Ile Gly Asn Glu Thr Ala Val Asn Val Asp Ser Ser His Thr Glu
                    565                 570                 575

TAT ACA TTG TCC TCT TTG ACT AGT GAC ACA TTG TAC ATG GTA CGA ATG        1776
Tyr Thr Leu Ser Ser Leu Thr Ser Asp Thr Leu Tyr Met Val Arg Met
            580                 585                 590

GCA GCA TAC ACA GAT GAA GGT GGG AAG GAT GGT CCA GAA TTC ACT TTT        1824
Ala Ala Tyr Thr Asp Glu Gly Gly Lys Asp Gly Pro Glu Phe Thr Phe
        595                 600                 605

ACT ACC CCA AAG TTT GCT CAA GGA GAA ATT GAA GCC ATA GTC GTG CCT        1872
Thr Thr Pro Lys Phe Ala Gln Gly Glu Ile Glu Ala Ile Val Val Pro
610                 615                 620

GTT TGC TTA GCA TTC CTA TTG ACA ACT CTT CTG GGA GTG CTG TTC TGC        1920
Val Cys Leu Ala Phe Leu Leu Thr Thr Leu Leu Gly Val Leu Phe Cys
625                 630                 635                 640

TTT AAT AAG CGA GAC CTA ATT AAA AAA CAC ATC TGG CCT AAT GTT CCA        1968
Phe Asn Lys Arg Asp Leu Ile Lys Lys His Ile Trp Pro Asn Val Pro
                    645                 650                 655

GAT CCT TCA AAG AGT CAT ATT GCC CAG TGG TCA CCT CAC ACT CCT CCA        2016
Asp Pro Ser Lys Ser His Ile Ala Gln Trp Ser Pro His Thr Pro Pro
            660                 665                 670

AGG CAC AAT TTT AAT TCA AAA GAT CAA ATG TAT TCA GAT GGC AAT TTC        2064
Arg His Asn Phe Asn Ser Lys Asp Gln Met Tyr Ser Asp Gly Asn Phe
        675                 680                 685

ACT GAT GTA AGT GTT GTG GAA ATA GAA GCA AAT GAC AAA AAG CCT TTT        2112
Thr Asp Val Ser Val Val Glu Ile Glu Ala Asn Asp Lys Lys Pro Phe
690                 695                 700

CCA GAA GAT CTG AAA TCA TTG GAC CTG TTC AAA AAG GAA AAA ATT AAT        2160
Pro Glu Asp Leu Lys Ser Leu Asp Leu Phe Lys Lys Glu Lys Ile Asn
705                 710                 715                 720

ACT GAA GGA CAC AGC AGT GGT ATT GGG GGT TCT TCA TGC ATG TCA TCT        2208
Thr Glu Gly His Ser Ser Gly Ile Gly Gly Ser Ser Cys Met Ser Ser
                    725                 730                 735

TCT AGG CCA AGC ATT TCT AGC AGT GAT GAA AAT GAA TCT TCA CAA AAC        2256
Ser Arg Pro Ser Ile Ser Ser Ser Asp Glu Asn Glu Ser Ser Gln Asn
            740                 745                 750

ACT TCG AGC ACT GTC CAG TAT TCT ACC GTG GTA CAC AGT GGC TAC AGA        2304
Thr Ser Ser Thr Val Gln Tyr Ser Thr Val Val His Ser Gly Tyr Arg
        755                 760                 765

CAC CAA GTT CCG TCA GTC CAA GTC TTC TCA AGA TCC GAG TCT ACC CAG        2352
His Gln Val Pro Ser Val Gln Val Phe Ser Arg Ser Glu Ser Thr Gln
770                 775                 780

CCC TTG TTA GAT TCA GAG GAG CGG CCA GAA GAT CTA CAA TTA GTA GAT        2400
Pro Leu Leu Asp Ser Glu Glu Arg Pro Glu Asp Leu Gln Leu Val Asp
785                 790                 795                 800

CAT GTA GAT GGC GGT GAT GGT ATT TTG CCC AGG CAA CAG TAC TTC AAA        2448
His Val Asp Gly Gly Asp Gly Ile Leu Pro Arg Gln Gln Tyr Phe Lys
                    805                 810                 815

CAG AAC TGC AGT CAG CAT GAA TCC AGT CCA GAT ATT TCA CAT TTT GAA        2496
Gln Asn Cys Ser Gln His Glu Ser Ser Pro Asp Ile Ser His Phe Glu
            820                 825                 830

AGG TCA AAG CAA GTT TCA TCA GTC AAT GAG GAA GAT TTT GTT AGA CTT        2544
Arg Ser Lys Gln Val Ser Ser Val Asn Glu Glu Asp Phe Val Arg Leu
        835                 840                 845
```

```
AAA CAG CAG ATT TCA GAT CAT ATT TCA CAA TCC TGT GGA TCT GGG CAA     2592
Lys Gln Gln Ile Ser Asp His Ile Ser Gln Ser Cys Gly Ser Gly Gln
    850                 855                 860

ATG AAA ATG TTT CAG GAA GTT TCT GCA GCA GAT GCT TTT GGT CCA GGT     2640
Met Lys Met Phe Gln Glu Val Ser Ala Ala Asp Ala Phe Gly Pro Gly
865                 870                 875                 880

ACT GAG GGA CAA GTA GAA AGA TTT GAA ACA GTT GGC ATG GAG GCT GCG     2688
Thr Glu Gly Gln Val Glu Arg Phe Glu Thr Val Gly Met Glu Ala Ala
                885                 890                 895

ACT GAT GAA GGC ATG CCT AAA AGT TAC TTA CCA CAG ACT GTA CGG CAA     2736
Thr Asp Glu Gly Met Pro Lys Ser Tyr Leu Pro Gln Thr Val Arg Gln
            900                 905                 910

GGC GGC TAC ATG CCT CAG                                             2754
Gly Gly Tyr Met Pro Gln
            915
```

(2) INFORMATION FOR SEQ ID NO:6:

(i) SEQUENCE CHARACTERISTICS:
        (A) LENGTH: 918 amino acids
        (B) TYPE: amino acid
        (D) TOPOLOGY: linear (ii) MOLECULE TYPE: protein (xi) SEQUENCE DESCRIPTION: SEQ ID NO:6:

```
Met Leu Thr Leu Gln Thr Trp Val Val Gln Ala Leu Phe Ile Phe Leu
 1               5                  10                  15

Thr Thr Glu Ser Thr Gly Glu Leu Leu Asp Pro Cys Gly Tyr Ile Ser
                20                  25                  30

Pro Glu Ser Pro Val Val Gln Leu His Ser Asn Phe Thr Ala Val Cys
            35                  40                  45

Val Leu Lys Glu Lys Cys Met Asp Tyr Phe His Val Asn Ala Asn Tyr
        50                  55                  60

Ile Val Trp Lys Thr Asn His Phe Thr Ile Pro Lys Glu Gln Tyr Thr
 65                  70                  75                  80

Ile Ile Asn Arg Thr Ala Ser Ser Val Thr Phe Thr Asp Ile Ala Ser
                85                  90                  95

Leu Asn Ile Gln Leu Thr Cys Asn Ile Leu Thr Phe Gly Gln Leu Glu
            100                 105                 110

Gln Asn Val Tyr Gly Ile Thr Ile Ile Ser Gly Leu Pro Pro Glu Lys
        115                 120                 125

Pro Lys Asn Leu Ser Cys Ile Val Asn Glu Gly Lys Lys Met Arg Cys
    130                 135                 140

Glu Trp Asp Gly Gly Arg Glu Thr His Leu Glu Thr Asn Phe Thr Leu
145                 150                 155                 160

Lys Ser Glu Trp Ala Thr His Lys Phe Ala Asp Cys Lys Ala Lys Arg
                165                 170                 175

Asp Thr Pro Thr Ser Cys Thr Val Asp Tyr Ser Thr Val Tyr Phe Val
            180                 185                 190

Asn Ile Glu Val Trp Val Glu Ala Glu Asn Ala Leu Gly Lys Val Thr
        195                 200                 205

Ser Asp His Ile Asn Phe Asp Pro Val Tyr Lys Val Lys Pro Asn Pro
    210                 215                 220

Pro His Asn Leu Ser Val Ile Asn Ser Glu Glu Leu Ser Ser Ile Leu
225                 230                 235                 240

Lys Leu Thr Trp Thr Asn Pro Ser Ile Lys Ser Val Ile Ile Leu Lys
                245                 250                 255
```

```
Tyr Asn Ile Gln Tyr Arg Thr Lys Asp Ala Ser Thr Trp Ser Gln Ile
            260                 265                 270

Pro Pro Glu Asp Thr Ala Ser Thr Arg Ser Ser Phe Thr Val Gln Asp
        275                 280                 285

Leu Lys Pro Phe Thr Glu Tyr Val Phe Arg Ile Arg Cys Met Lys Glu
        290                 295                 300

Asp Gly Lys Gly Tyr Trp Ser Asp Trp Ser Glu Ala Ser Gly Ile
305                 310                 315                 320

Thr Tyr Glu Asp Arg Pro Ser Lys Ala Pro Ser Phe Trp Tyr Lys Ile
                325                 330                 335

Asp Pro Ser His Thr Gln Gly Tyr Arg Thr Val Gln Leu Val Trp Lys
                340                 345                 350

Thr Leu Pro Pro Phe Glu Ala Asn Gly Lys Ile Leu Asp Tyr Glu Val
            355                 360                 365

Thr Leu Thr Arg Trp Lys Ser His Leu Gln Asn Tyr Thr Val Asn Ala
            370                 375                 380

Thr Lys Leu Thr Val Asn Leu Thr Asn Asp Arg Tyr Leu Ala Thr Leu
385                 390                 395                 400

Thr Val Arg Asn Leu Val Gly Lys Ser Asp Ala Ala Val Leu Thr Ile
                405                 410                 415

Pro Ala Cys Asp Phe Gln Ala Thr His Pro Val Met Asp Leu Lys Ala
                420                 425                 430

Phe Pro Lys Asp Asn Met Leu Trp Val Glu Trp Thr Thr Pro Arg Glu
            435                 440                 445

Ser Val Lys Lys Tyr Ile Leu Glu Trp Cys Val Leu Ser Asp Lys Ala
        450                 455                 460

Pro Cys Ile Thr Asp Trp Gln Gln Glu Asp Gly Thr Val His Arg Thr
465                 470                 475                 480

Tyr Leu Arg Gly Asn Leu Ala Glu Ser Lys Cys Tyr Leu Ile Thr Val
                485                 490                 495

Thr Pro Val Tyr Ala Asp Gly Pro Gly Ser Pro Glu Ser Ile Lys Ala
            500                 505                 510

Tyr Leu Lys Gln Ala Pro Pro Ser Lys Gly Pro Thr Gly Arg Thr Lys
        515                 520                 525

Lys Val Gly Lys Asn Glu Ala Val Leu Glu Trp Asp Gln Leu Pro Val
        530                 535                 540

Asp Val Gln Asn Gly Phe Ile Arg Asn Tyr Thr Ile Phe Tyr Arg Thr
545                 550                 555                 560

Ile Ile Gly Asn Glu Thr Ala Val Asn Val Asp Ser Ser His Thr Glu
                565                 570                 575

Tyr Thr Leu Ser Ser Leu Thr Ser Asp Thr Leu Tyr Met Val Arg Met
            580                 585                 590

Ala Ala Tyr Thr Asp Glu Gly Gly Lys Asp Gly Pro Glu Phe Thr Phe
            595                 600                 605

Thr Thr Pro Lys Phe Ala Gln Gly Glu Ile Glu Ala Ile Val Val Pro
        610                 615                 620

Val Cys Leu Ala Phe Leu Leu Thr Thr Leu Leu Gly Val Leu Phe Cys
625                 630                 635                 640

Phe Asn Lys Arg Asp Leu Ile Lys Lys His Ile Trp Pro Asn Val Pro
                645                 650                 655

Asp Pro Ser Lys Ser His Ile Ala Gln Trp Ser Pro His Thr Pro Pro
                660                 665                 670

Arg His Asn Phe Asn Ser Lys Asp Gln Met Tyr Ser Asp Gly Asn Phe
```

|   |   |   | 675 |   |   |   | 680 |   |   |   | 685 |   |
|---|---|---|---|---|---|---|---|---|---|---|---|---|

Thr Asp Val Ser Val Val Glu Ile Glu Ala Asn Asp Lys Lys Pro Phe
            690                 695                 700

Pro Glu Asp Leu Lys Ser Leu Asp Leu Phe Lys Lys Glu Lys Ile Asn
705                 710                 715                 720

Thr Glu Gly His Ser Ser Gly Ile Gly Gly Ser Ser Cys Met Ser Ser
                725                 730                 735

Ser Arg Pro Ser Ile Ser Ser Asp Glu Asn Glu Ser Ser Gln Asn
            740                 745                 750

Thr Ser Ser Thr Val Gln Tyr Ser Thr Val Val His Ser Gly Tyr Arg
            755                 760                 765

His Gln Val Pro Ser Val Gln Val Phe Ser Arg Ser Glu Ser Thr Gln
            770                 775                 780

Pro Leu Leu Asp Ser Glu Glu Arg Pro Glu Asp Leu Gln Leu Val Asp
785                 790                 795                 800

His Val Asp Gly Gly Asp Gly Ile Leu Pro Arg Gln Gln Tyr Phe Lys
                805                 810                 815

Gln Asn Cys Ser Gln His Glu Ser Ser Pro Asp Ile Ser His Phe Glu
            820                 825                 830

Arg Ser Lys Gln Val Ser Ser Val Asn Glu Glu Asp Phe Val Arg Leu
            835                 840                 845

Lys Gln Gln Ile Ser Asp His Ile Ser Gln Ser Cys Gly Ser Gly Gln
850                 855                 860

Met Lys Met Phe Gln Glu Val Ser Ala Ala Asp Ala Phe Gly Pro Gly
865                 870                 875                 880

Thr Glu Gly Gln Val Glu Arg Phe Glu Thr Val Gly Met Glu Ala Ala
            885                 890                 895

Thr Asp Glu Gly Met Pro Lys Ser Tyr Leu Pro Gln Thr Val Arg Gln
            900                 905                 910

Gly Gly Tyr Met Pro Gln
            915

(2) INFORMATION FOR SEQ ID NO:7:

(i) SEQUENCE CHARACTERISTICS:
        (A) LENGTH: 17 base pairs
        (B) TYPE: nucleic acid
        (C) STRANDEDNESS: both
        (D) TOPOLOGY: linear (ii) MOLECULE TYPE: cDNA (xi) SEQUENCE DESCRIPTION: SEQ ID NO:7:

CCGCAGGTCG AGACAGC                                  17

(2) INFORMATION FOR SEQ ID NO:8:

(i) SEQUENCE CHARACTERISTICS:
        (A) LENGTH: 18 base pairs
        (B) TYPE: nucleic acid
        (C) STRANDEDNESS: both
        (D) TOPOLOGY: linear (ii) MOLECULE TYPE: cDNA (xi) SEQUENCE DESCRIPTION: SEQ ID NO:8:

CAAACACCTT CTCGCGAA                               18

(2) INFORMATION FOR SEQ ID NO:9:

(i) SEQUENCE CHARACTERISTICS:
    (A) LENGTH: 19 base pairs
    (B) TYPE: nucleic acid
    (C) STRANDEDNESS: both
    (D) TOPOLOGY: linear (ii) MOLECULE TYPE: cDNA (xi) SEQUENCE DESCRIPTION: SEQ ID NO:9:

CTTCAGGGAG AGCGCGTGC                                                    19

(2) INFORMATION FOR SEQ ID NO:10:

(i) SEQUENCE CHARACTERISTICS:
        (A) LENGTH: 20 base pairs
        (B) TYPE: nucleic acid
        (C) STRANDEDNESS: both
        (D) TOPOLOGY: linear (ii) MOLECULE TYPE: cDNA (xi) SEQUENCE DESCRIPTION: SEQ ID NO:10:

TCATCAGGAC CCAGCTGTGC                                                   20

(2) INFORMATION FOR SEQ ID NO:11:

(i) SEQUENCE CHARACTERISTICS:
        (A) LENGTH: 21 base pairs
        (B) TYPE: nucleic acid
        (C) STRANDEDNESS: both
        (D) TOPOLOGY: linear (ii) MOLECULE TYPE: cDNA (xi) SEQUENCE DESCRIPTION: SEQ ID NO:11:

TTGACTAGTG ACACATTGTA C                                                 21

(2) INFORMATION FOR SEQ ID NO:12:

(i) SEQUENCE CHARACTERISTICS:
        (A) LENGTH: 20 base pairs
        (B) TYPE: nucleic acid
        (C) STRANDEDNESS: both
        (D) TOPOLOGY: linear (ii) MOLECULE TYPE: cDNA (xi) SEQUENCE DESCRIPTION: SEQ ID NO:12:

TGAAACTTGC TTTGACCTTT                                                   20

(2) INFORMATION FOR SEQ ID NO:13:

(i) SEQUENCE CHARACTERISTICS:
        (A) LENGTH: 20 base pairs
        (B) TYPE: nucleic acid
        (C) STRANDEDNESS: both
        (D) TOPOLOGY: linear (ii) MOLECULE TYPE: cDNA (xi) SEQUENCE DESCRIPTION: SEQ ID NO:13:

GGTACGAATG GCAGCATACA                                                   20

(2) INFORMATION FOR SEQ ID NO:14:

(i) SEQUENCE CHARACTERISTICS:
        (A) LENGTH: 20 base pairs
        (B) TYPE: nucleic acid
        (C) STRANDEDNESS: both
        (D) TOPOLOGY: linear

```
    (ii) MOLECULE TYPE: cDNA (xi) SEQUENCE DESCRIPTION: SEQ ID NO:14:

CTGGACTGGA TTCATGCTGA                                                    20
```

GP 130 LACKING THE TRANSMEMBRANE DOMAIN

CROSS-REFERENCE TO RELATED APPLICATIONS

This application is a continuation of PCT Application No. PCT/GB95/02243, filed Sep. 21, 1995, now abandoned.

FIELD OF THE INVENTION

The present invention relates to a novel human gp130 protein, DNA sequences coding for this protein, its use in therapy, particularly in in vitro fertilisation, as well as pharmaceutical formulations comprising such a protein.

BACKGROUND OF THE INVENTION

Successful embryo implantation requires correct development of the pre-implantation embryo, resulting in a hatched blastocyst which is able to implant into receptive endometrium. A considerable body of data has been collected which supports the idea that soluble growth factors, if secreted by the uterine epithelium, act directly on the embryo to control this process (Anderson, E. D., *J. Cellular Biochem.*, 53: 280–287 (1993) and Schultz, G. A. and Hevner, S., *Mutat Res.*, 296: 17–31 (992)).

In addition, developing embryos have been shown to produce a variety of cytokines which may act in an autocrine fashion on the endometrium to influence its receptivity. Examples of growth factors shown to be produced by human embryos include IL-1, IL-6, CSF-1 and TNF-α (Zolti et al, *Fertil. Steril.*, 56 (1991) 265–272 and Witkin et al, *J. Reprod. Immunol.*, 19 (1991) 85–93). TNF-α has been shown to be present in culture medium of human embryos up to the morula stage, but not that from the blastocyst (Lachappelle et al, *Human Reproduction*, 8: 1032–1038 (1993)). Production of cytokines by the embryo may therefore be regulated in a stage-specific manner.

Data on the possible direct effects of cytokines on embryos have come primarily from experiments in mice where many cytokines have been shown to affect the development of preimplantation embryos in vitro. RFN-γ and CSF-1, at physiological concentrations, inhibit the number of embryos developing to the blastocyst stage (Hill et al, *J. Immunol.*, 139 (1987) 2250–2254). TNF-α has also been shown to have more subtle effects. Although TNF-α has no apparent effect on rates of blastocyst formation, it appears to specifically inhibit proliferation of cells contributing to the inner cell mass (ICM), which results in blastocysts with a reduced ICM (Pampfer et al, *Endocrinology*, 134: 206–212 (1994)).

Other growth factors also have specific effects on ICM cells. For instance, insulin-like growth factors 1 and 2 stimulate ICM proliferation, whereas leukaemia inhibitory factor (LIF) inhibits their differentiation (Harvey et al, *Mol. Reprod. Dev.*, 31 (1992) 195–199).

As mentioned above, IL-6 is one of the growth factors which has been shown to be produced by human embryos. IL-6 is a protein which controls the proliferation and differentiation of many cell types in mammals, and in addition has a role in the control of the immune system. Binding of IL-6 to IL-6R initiates the association of IL-6R with a third component known as gp130, which actually transmits the signal through the cell membrane (Taga et al, *PNAS*, 89: 10998–11001). gp130 is a transmembrane protein, i.e. it extends through the membrane and projects into the cytoplasm, thus it has distinct domains. In this way, IL-6 "signal" transmission is mediated by means of this protein.

EP-A-0411946 discloses a recombinant gp130 protein, as well as DNA sequences coding for such a protein and methods for its cloning.

Yasukawa et al, *Immunology Letters*, 31 (1992) 123–130, discloses a soluble, recombinant form of gp130, produced by removing the transmembrane and cytoplasmic regions of the membrane bound form of the protein.

Narazaki et al, *Blood.*, 82, No 4 (1993) 1120–1126, disclosed that soluble forms of gp130 exist and may have potential to inhibit signals normally mediated by transmembrane gp130.

SUMMARY OF THE INVENTION

The present invention relates to a novel human gp130 protein, DNA sequences coding for this protein, its use in therapy, particularly in in vitro fertilization, as well as pharmaceutical compositions comprising such a protein.

The invention also relates to an isolated and substantially purified gp130 encoded by a DNA sequence.

The invention further relates to the use of gp130 to antagonize the action of one or more growth factors, wherein the growth factors are one or more of IL-6, LIF, CNTF, Oncostatin M or IL-II.

The invention also relates to the use of gp130 to ensure the correct development of pre-implantation embryos.

The invention further relates to a pharmaceutical composition comprising gp130 together with pharmaceutically acceptable excipients. The invention also relates to the use of this pharmaceutical composition for antagonizing the action of one or more growth factors. The invention further relates to the use of this pharmaceutical composition for ensuring the correct development of pre-implantation embryos.

The invention also relates to a method for antagonizing the action of one or more growth factors in a pre-implantation embryo which comprises the step of administering to the embryo gp130.

DESCRIPTION OF THE PREFERRED EMBODIMENTS

There has now been found a novel form of gp130, lacking the transmembrane portion, which form arises by means of alternative splicing of the sequence coding for the transmembrane gp130. This form of gp130 may bind to complexes of, for example, IL-6 receptor, resulting in a blocking of the association of the complex with transmembrane gp130.

The novel splicing pattern, as well as resulting in loss of the transmembrane domain, also results in a frameshift, leading to 45 new amino acids before an in frame stop codon.

Thus, the present invention provides gp130 which includes the following C-terminal sequence (SEQ ID NO:1):

```
Glu Leu Lys Asn Thr Ser Gly Leu Met Phe Gln Ile Leu

Gln Arg Val Ile Leu Pro Ser Gly His Leu Thr Leu Leu

Gln Gly Thr Ile Leu Ile Gln Lys Ile Lys Cys Ile Gln

Met Ala Ile Ser Leu Met
``` or a C-terminal sequence which is substantially homologous thereto.

Preferably, the novel gp130 of the invention has the above-noted sequence from amino acid position 614. In one embodiment the novel gp130 of the invention has a sequence at positions 1–613 substantially homologous to that shown in FIG. 2 (SEQ ID NO:6).

At the amino acid level, a protein sequence may be regarded as substantially homologous to another protein sequence if a significant number of the constituent amino acids exhibit homology. At least 40%, 50%, 60%, 70%, 80%, 90%, 95% or even 99%, in increasing order of preference, of the amino acids may be homologous.

Thus, activation of the alternative splicing mechanism can result in the production of a novel gp130 in human blastocysts, resulting in inactivation of the effects of, for example, LIF, which in turn may allow differentiation of the inner cell mass, allowing ICM differentiation to proceed. Clearly, therefore, the novel gp130 of the invention can be used in the treatment of preimplantation embryos to ensure correct differentiation and development prior to implantation in a subject.

In addition, the invention also provides a DNA sequence coding for a protein of the invention which sequence includes a sequence substantially homologous to (SEQ ID NO:2):

```
GAA TTA AAA AAC ACA TCT GGC CTA ATG TTC CAG ATC CTT

CAA AGA GTC ATA TTG CCC AGT GGT CAC CTC ACA CTC CTC

CAA GGC ACA ATT TTA ATT CAA AAG ATC AAA TGT ATT CAG

ATG GCA ATT TCA CTG ATG TAA
```

"DNA sequence substantially the same" includes all other nucleic acid sequences which, by virtue of the degeneracy of the genetic code, also code for the given amino acid sequence or which are substantially homologous to such a sequence.

Sequences having substantial homology may be regarded as those which will hybridise to the nucleic acid sequence shown in FIG. 2 (SEQ ID NO:5) under stringent conditions (for example, at 35 to 65° C. in a salt solution of about 0.9M)

DNA constructs comprising DNA sequences of the invention form another aspect of the present invention.

As discussed herein, the protein of the invention is useful in antagonising the action of certain growth factors, thus enabling certain development processes to be "switched on" in preimplantation embryos. Thus, in a further aspect, the present invention provides the use of the protein of the invention in antagonising the action of one or more growth factors, including IL-6, Leukaemia Inhibitory Factor (LIF), Oncostatin Myciliary Neurotrophic Factor (CNTF) and IL-II.

In addition, the invention also provides the use of the protein of the invention in the manufacture of a medicament for use in ensuring correct development in preimplantation embryos. Preferably, the medicament is used to ensure that differentiation of the ICM commences at the correct time.

The medicament is preferably presented in the form of a pharmaceutical formulation comprising the protein of the invention together with one or more pharmaceutically acceptable carriers and/or excipients. Such pharmaceutical formulations form a yet further aspect of the present invention.

A final aspect of the present invention provides a method for antagonising the action of one or more growth factors which comprises the step of treating a pre-implantation embryo with the protein of the present invention, preferably in the form of a pharmaceutical formulation. Preferably the invention provides a method for ensuring correct development of a preimplantation embryo.

The invention will now be described by means of the following examples, which examples should not be construed as in any way limiting the present invention. The examples refer to the following figures which show:

BRIEF DESCRIPTION OF THE DRAWINGS

FIG. 1: the sequence of the soluble gp130 (SEQ ID NO:4) and a DNA sequence (SEQ ID NO:3) coding for it;

FIG. 2: the sequence of native gp130 (SEQ ID NO:5 and 6);

FIG. 3: agarose gel showing the products of nested RT-PCR amplification on RNA from human embryos. Each panel shows the products of amplification with primers specific for different cDNA targets. Amplified cDNAs from different embryos were loaded in each lane. Lanes are labelled according to cDNA labels in Table 1 (below). Additional samples were: lane p, first trimester trophoblast; lane q, cDNA from 200 BeWO cells; lane r, 10 ng human genomic DNA; and lane s, no input cDNA, as a negative control. DNA molecular weight markers were a 123 base pair ladder loaded in lane i. The sizes of the expected PCR products are shown in bp.

TABLE 1

| Human embryo cDNAs and controls name stage of development | |
|---|---|
| a | 2 cell |
| b | 3 cell |
| c | 4 cell |
| d | 6 cell |
| e | 8 cell |
| f | monila |
| g | blastocyst |
| h | culture supernatant for a to g |
| j | three pooled blastocysts |
| k | culture supernatant for j |
| l | 2 × 6 cell and 1 × 8 cell |
| m | culture supernatant for l |
| n | 1 × 4 cell and 1 × 6 cell |
| o | culture supernatant for n | samples a to h are from the same donor.

FIG. 4: primers used for RT-PCR (SEQ ID NOS:7 through 14).

EXAMPLES

Example 1

Embryo Culture and RNA Extraction

Crypopreserved human embryos which had been fertilised as part of an IVF program were used in this study. These embryos had been donated for research purposes by the parents and this study complied with the requirements of the Human Embryology and Fertilisation Authority, and the local ethical committee. Frozen embryos were thawed and cultured in Earles balanced salts medium supplemented with 0.4% human serum albumin (Armour Pharmaceuticals UK), until the required developmental stage, then flash frozen in liquid nitrogen in 5 μl of culture fluid (and thus lysed by ice crystals). An identical volume of culture supernatant was frozen as a control. Any remaining cumulus cells were removed during routine handling.

Total RNA from first trimester trophoblast was isolated by the method of Chomsczynski and Sacchi, *Anal. Biochem.*, 162: 156–159 (1987) in which frozen tissue is homogenised in 5 ml of buffer containing 4 M guanidinium thiocyanate (Gibco BRL Livingston, Scotland), 25 mM sodium citrate pH 7.0, 0.5% sarcosyl and 0.1 M 2-mercaptoethanol. The lysate was acidified by the addition of 0.5 ml of 2 M sodium acetate pH 4, and phenol-chloroform extracted using 5 ml of buffer saturated phenol and 1 ml chloroform-isoamylalcohol (49:1 v/v). The suspension was placed on ice for 15 minutes and centrifuged at 10,000 g for 20 minutes at 4° C. The aqueous phase containing RNA was precipitated, washed twice in 70% ethanol, dried and resuspended in TE (10 mM Tris-HCl pH 7.4 and 1 mM EDTA). The concentration of RNA was determined spectrophotometrically at 260 nm.

RNA was prepared from single human embryos using a scaled down protocol based on the above procedure. To assist precipitation of the RNA 100 μg of carrier yeast tRNA (Gibco BRL, Livingston, Scotland) was added at the homogenisation step. The remaining details are as described above, except that all the volumes were 50 fold less and the whole procedure was carried out in 400 μl Eppendorf tubes.

Example 2

Reverse Transcriptase Polymerase Chain Reaction (RT-PCR)

cDNA was synthesised from half the total RNA from each embryo using AMV reverse transcriptase (Super RT, HT Biotech, Cambridge, UK). 3–5 micrograms of RNA was primed with oligo dT (Pharmacia), according to the manufacturers instructions for 60 minutes at 42° C. PCR amplification of the cDNA preparations was performed as previously described (Sharkey, A. et al, *Molecular Endocrinol.*, 6: 1235–1241 (1992)) with a Hybaid Omnigene DNA thermal cycler in a final volume of 30 μl using 1 U of Taq DNA polymerase (Cetus, Emeryville, Calif.) and 10 μM of each of the pair of external primers (see FIG. 4) in the manufacturer's recommended buffer. The following cycle profile was used: 30s at 95° C., 30s at X° C. , 30s at 72° C. for 30 cycles, where X is the annealing temperature for each pair of cytokine primers.

|  | External Primers (° C.) | Internal Primers (° C.) |
| --- | --- | --- |
| gp130 | 49 | 54 |
| HistRNA | 52 | 59 |

Oligonucleotide primers

Oligonucleotide primers for gp130 and HistidylRNA synthetase were synthesised on a Cruachem PS250 DNA synthesiser. Primer sequences were designed from published nucleotide sequences (see FIG. 4), such that amplification of any contaminating genomic DNA would result in a differently sized product from the cDNA species.

Because of the small amount of material, two pairs of primers were used for each target cDNA, in a nested PCR protocol. One thirtieth of the cDNA products were amplified using Amplitaq (Cetus), in the manufacturers recommended buffer. Following 30 cycles of PCR using the external primer pair, one fiftieth of the first round reaction was transferred to a fresh tube containing the inner primer pair, and subjected to a further 30 rounds of amplification. As negative control, an equal volume of the culture fluid in which the embryo was grown was extracted and subjected to RT-PCR in the same way. Also, 200 cells of the BeWo cell line (ECACC No 86082803) were extracted as positive control.

The primers used in this study are shown in FIG. 4, together with the size of the expected product. The identity of each product was confirmed by cloning and sequencing as described previously (Sharkey et al, *Mol. Endocrinol.* (1992)). To ensure that the product detected resulted from amplification of cDNA rather than contaminating genomic DNA, primers were chosen to cross intron/exon boundaries. Ten nanograms of genomic DNA was also subjected to PCR at the same time as the cDNA to verify no product of the expected size resulted from genomic DNA.

RESULTS

The technique of RT-PCR was applied to total RNA extracted from human embryos produced by in vitro fertilisation. Embryos were cultured to the appropriate stage, then quick-frozen in liquid nitrogen. Stored embryos were thawed and total RNA extracted. In order to produce detectable RT-PCR product from total RNA extracted from a single embryo, a nested PCR protocol was employed in which the cDNA was subjected to two sets of PCR amplification with an external primer pair, followed by an internal pair. Primers were based on published cDNA sequences and designed to span intron-exon boundaries so that amplification of contaminating genomic DNA could be readily distinguished from cDNA products.

Initially, cDNA from each embryo was tested with primers for histidyl tRNA synthetase (HistRS) to confirm successful RNA isolation and reverse transcription. The primers used gave rise to weak products of greater than 400 bp from genomic DNA and 110 bp from cDNA derived from HistRS MRNA. Transcripts for Hist RS were detected in MRNA from embryos at all stages of development, as well as in decidua and the choriocarcinoma cell line BeWo, used as positive controls (FIG. 3, lanes p and q respectively). No product was detected in an equal volume of embryo culture supernatant extracted and subjected co RT-PCR in the same way, indicating that there was no contamination of the culture with extraneous CDNA or RNA.

Examples of similar RT-PCR analysis with primers for gp130 are shown in FIG. 3. Stocks of cDNA were reverse transcribed from each RNA sample on two separate occasions and the PCR assays were repeated twice on each cDNA stock. The results are shown in FIG. 3, which displays phe pattern of expression of gp130 during preimDlantation development. The identity of the PCR fragment of the correct size was confirmed by sequencing of the cloned PCR product. In cases where novel sized products were seen, these were also cloned and sequenced.

For gp130, the Predicted fragment is 712 bp. However, during the morula to blastocyst transition, a novel, smaller transcript was detected of approximately 600 bp. This result appeared consistent since, in sample j, which derives from cDNA made from 3 pooled blastocysts, both products were detected simultaneously. Upon cloning and sequencing, the smaller product appeared to arise due to an alternative splicing event which removes the exon encoding the transmembrane domain. The predicted sequence of the novel transcript is shown in FIG. 1. The novel splicing pattern also involves a frameshift, resulting in 45 new amino acids, before an in frame stop codon.

DISCUSSION

Many growth factors have been shown to influence the development of cultured preimplantation mammalian embryos (for review see Anderson, E. D., *J. Cellular Biochem.*, 53: 280–287 (1993) and Schultz, G. A. and Hevner, S., *Mutat Res.*, 296: 17–31 (1992)).

However, there is good evidence for species to species differences in expression of growth factor receptors in preimplantation development. For instance, EGF mRNA is expressed in the pig embryo but has not been found at any stage in mouse preimDlantation embryos (Vaughan et al, *Development*, 116: 663–669 (1992); Rapolee et al, *Science*, 241: 1823–1825 (1988); and Watson, A. J. et al, *Biol. Reprod.*, 50: 725–733 (1994)). Therefore the usefulness of these studies to researchers interested in factors controlling human preimplantation development is limited. In addition, the specific growth factors and receptors investigated in such studies frequently have been chosen on an ad hoc basis. Both for ethical and practical reasons, such an approach is not suitable for use with human embryos. We have therefore used a nested RT-PCR method which has allowed us to screen for the expression of growth factor and receptor mRNAs in single human preimplantation embryos. This method has been widely is used over the last few years in other species since it is reliable, sensitive and economical in its use of embryo material.

RT-PCR with primers for Histidyl-tRNA synthetase was used on cDNA samples to confirm that cDNA had been successfully prepared form each embryo RNA sample. cDNA specific for this housekeeping gene was successfully detected in cDNA samples made even from a single 2-cell embryo, indicating that the method was sufficiently sensitive for this study.

We found that during the morula to blastocyst transition, the size of the gp130 PCR product decreased by about 100 bp. Sequencing of the smaller product indicated that it results from a novel splice variant of the gp130 mRNA. This new splice variant lacks the transmembrane domain, and would be expected to produce a novel form of gp130. Soluble gp130 protein has recently been detected in human serum and has been shown to antagonise the action of IL-6 and LIFR. When the cytokines associate with their respective receptors, soluble gp130 is able to bind to this complex, blocking association with membrane bound gp130. The possibility is that selective expression of the novel gp130 in the blastocoel cavity in the late blastocyst stage would inactivate the effects of LIF in preventing differentiation of the linear cell mass, allowing ICM differentiation to proceed.

We claim:

1. An isolated and substantially purified DNA coding for a protein having the amino acid sequence of SEQ ID NO:4.

2. The DNA as claimed in claim 1 which hybridises under stringent conditions of between 35° C. to 65° C. and a salt concentration of about 0.9 M to the DNA sequence of SEQ ID NO:3.

3. A recombiant DNA comprising DNA as defined in claim 1 or claim 2.

* * * * *